US009644234B2

(12) United States Patent
Pipper et al.

(10) Patent No.: US 9,644,234 B2
(45) Date of Patent: May 9, 2017

(54) METHODS AND DEVICE TO BALANCE RADIATION TRANSFERENCE

(71) Applicant: Agency for Science, Technology and Research, Singapore (SG)

(72) Inventors: Juergen Hans Pipper, Singapore (SG); Sankar Thulasinga, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/368,420

(22) PCT Filed: Dec. 28, 2012

(86) PCT No.: PCT/SG2012/000492
§ 371 (c)(1),
(2) Date: Jun. 24, 2014

(87) PCT Pub. No.: WO2013/100859
PCT Pub. Date: Jul. 4, 2013

(65) Prior Publication Data
US 2015/0031039 A1    Jan. 29, 2015

(30) Foreign Application Priority Data

Dec. 28, 2011    (SG) ................................ 201109702

(51) Int. Cl.
*C12Q 1/68* (2006.01)
*C12P 19/34* (2006.01)
(Continued)

(52) U.S. Cl.
CPC ................ *C12Q 1/686* (2013.01); *B01L 7/52* (2013.01); *H05B 7/18* (2013.01);
(Continued)

(58) Field of Classification Search
None
See application file for complete search history.

(56) References Cited

U.S. PATENT DOCUMENTS

| | | | |
|---|---|---|---|
| 5,113,479 A * | 5/1992 | Anderson | ........... B29C 35/0266 156/275.1 |
| 6,413,766 B2 | 7/2002 | Landers et al. | |
| 2003/0017551 A1 * | 1/2003 | Parthasarathy | ...... C12Q 1/6844 435/91.1 |
| 2005/0287661 A1 | 12/2005 | Landers | |
| 2010/0323923 A1 | 12/2010 | Corbett | |

FOREIGN PATENT DOCUMENTS

| | | |
|---|---|---|
| CN | 101160646 | 4/2008 |
| WO | WO 96/41864 | 12/1996 |
| WO | WO 2006/113100 | 10/2006 |

OTHER PUBLICATIONS

Lee et al., "Microchip-based one step DNA extraction and real-time PCR in one chamber for rapid pathogen identification," Lab Chip, 2006, vol. 6, pp. 886-895.*
(Continued)

*Primary Examiner* — Young J Kim
(74) *Attorney, Agent, or Firm* — Wolf, Greenfield & Sacks, P.C.

(57) ABSTRACT

A method and device for adjusting the temperature of a sample by heating a substrate with a laser diode light; said light projected on to the substrate to absorb the light and convert the light energy to a heat energy thereby raising the temperature of the substrate corresponding to the intensity of the light energy, the substrate configured to transfer the thermal energy substantially homogenously to the sample. The device or method suitable for amplification of a nucleic acid sample.

13 Claims, 17 Drawing Sheets

(51) Int. Cl.
*B01L 7/00* (2006.01)
*H05B 7/18* (2006.01)
(52) U.S. Cl.
CPC .............. *B01L 2300/1805* (2013.01); *B01L 2300/1861* (2013.01); *B01L 2300/1872* (2013.01)

(56) References Cited

OTHER PUBLICATIONS

Dou et al., Explosive boiling water films adjacent to heated surfaces: a microscopic description. J Phys Chem A. Aug 2, 2001;105:2748-55.
Kim et al., Nanodroplet real-time PCR system with laser assisted heating. Optics Express. Jan. 5, 2009;17(1):218-27.
Schieltz et al., Mass spectrometry of DNA mixtures by laser ablation from frozen aqueous solution. Rapid Commun Mass Spectrom. Oct. 1992;6(10):631-6.
Terazono et al., Rapid real-time PCT-based nucleotide sequence measurement method using 1480nm infrared laser heating. Microprocesses and Nanotechnology. Nov. 5-8, 2007:326-7.
Williams et al., Time of flight mass spectrometry of DNA laser-ablated from frozen aqueous solutions: applications to the Human Genome Project. International Journal of Mass Spectrometry and Ion Processes. Feb. 24, 1994;131:335-44.
Extended European Search Report dated Jul. 6, 2015 in connection with Application No. 12861881.6.

\* cited by examiner

| Setup[a] | ⊠ | ⊼ | ⊻ | -o- | ⊸ | ⊸ |
|---|---|---|---|---|---|---|
| | 4F@90° | 4F@120° | 3F@120° | 2F@180° | 2F@120° | 2F@90° |
| RPS[b] (Hz) | ΔT (°C) | ΔT (°C) | ΔT (°C) | ΔT (°C) | ΔT (°C) | ΔT (°C) |
| 0.14 | 0.27 | 0.31 | 0.29 | 0.83 | 0.88 | 0.93 |
| 0.3 | 0.23 | 0.31 | 0.37 | 1.99 | 0.85 | 1.01 |
| 0.4 | 0.19 | 0.27 | 0.33 | 1.54 | 0.92 | 1.76 |
| 0.6 | 0.11 | 0.20 | 0.23 | 1.24 | 1.27 | 1.39 |
| 1.11 | 0.05 | 0.11 | 0.07 | 0.24 | 0.40 | 0.41 |

[a] All beamlets are equivalent in output power
[b] Rounds per second

| Item/parameter | | T (°C) | I (A) | U (V) | Pi (W)[a] | t (s) | Pt (Wh)[b] | Cycles | |
|---|---|---|---|---|---|---|---|---|---|
| Laserdiode | Initial denaturation | rt⇗95 | 5.24 | 2.41 | 12.61 | 15.0 | 0.05 | 1 | |
| | | 95⇨ | 2.52 | 2.41 | 6.07 | 600.0 | 1.01 | 1 | |
| | Amplification | 60⇗95 | 5.34 | 2.41 | 12.88 | 7.0 | 1.25 | 50 | |
| | | 95⇨ | 2.82 | 2.41 | 6.79 | 5.0 | 0.47 | 50 | |
| | | 95⇘60 | 0.08 | 2.41 | 0.19 | 5.4 | 0.01 | 50 | |
| | | 60⇨ | 1.01 | 2.41 | 2.44 | 24.6 | 0.83 | 50 | |
| | Cooling | 60⇘rt | 0.08 | 2.41 | 0.19 | 30.0 | 0.00 | 1 | |
| Thermoelectric cooler[c] | Initial denaturation | rt⇗95 | 0.76 | 1.70 | 1.28 | 15.0 | 0.01 | 1 | |
| | | 95⇨ | 0.47 | 1.50 | 0.70 | 600.0 | 0.12 | 1 | |
| | Amplification | 60⇗95 | 0.59 | 1.70 | 1.01 | 7.0 | 0.10 | 50 | |
| | | 95⇨ | 0.79 | 1.50 | 1.19 | 5.0 | 0.08 | 50 | |
| | | 95⇘60 | 0.49 | 1.00 | 0.49 | 5.4 | 0.04 | 50 | |
| | | 95⇘60[d] | 0.24 | 5.00 | 1.20 | 5.4 | 0.09 | 50 | Fan |
| | | 60⇨ | 0.28 | 0.60 | 0.17 | 24.6 | 0.06 | 50 | |
| | Cooling | 60⇘rt | 0.24 | 5.00 | 1.20 | 30.0 | 0.01 | 1 | Fan |
| | | Power consumption per run | | | | | 4.13 | | |
| | | | | | | | 45.25 | min | |

[a] Instantaneous power
[b] Power over a one hour-period of time
[c] Thermoelectric cooler (TEC) as part of laserdiode high heatload (HHL) package
[d] Cooling Fan

Figure 4D

METHODS AND DEVICE TO BALANCE RADIATION TRANSFERENCE

CROSS-REFERENCE TO RELATED APPLICATION

This application claims benefit of, and priority from, Singapore patent application No. 201109702-9, filed on 28 Dec. 2011, the contents of which are hereby incorporated herein by reference.

FIELD

The invention relates to methods and device for heating and cooling biological material for analysis.

BACKGROUND

Multiplex polymerase chain reaction (Multiplex PCR) is a modification of PCR in order to rapidly detect deletions or duplications in a large gene. In this process, genomic nucleic acid samples are amplified using multiple primers and a temperature-mediated polymerase in a thermal cycler.

Multiplex-PCR consists of multiple primer sets within a single PCR mixture to produce amplicons of varying sizes that are specific to different DNA sequences. By targeting multiple genes at once, additional information may be gained from a single test run that otherwise would require several times the reagents and more time to perform. Annealing temperatures for each of the primer sets must be optimized to work correctly within a single reaction, and amplicon size, that is, their base pair length, should be different enough to form distinct bands when visualized by gel electrophoresis.

Commercial multiplexing kits for PCR are available and used by many forensic laboratories to amplify degraded DNA samples. Commercial kits have a number of advantages over in-house multiplexing methods. Quality control measures are undertaken by the manufacturer of the kit and ensure that reactions are uniform across all kits. This avoids the preparation of PCR master mixes which require pipetting and use of multiple assay tubes, increasing the risk of operator error and contamination. This increased reliability allows profiles obtained from commercial kits to be admitted into court which is pivotal in large criminal trials. The use of specific kits over a number of laboratories also allows for profile results to be compared as long as the same STR markers have been used in each kit.

Some of the applications of multiplex PCR include: Pathogen Identification; High Throughput SNP Genotyping; Mutation Analysis; Gene Deletion Analysis; Template Quantification; Linkage Analysis; RNA Detection; Forensic Studies. The current systems available are very big and heavy machines. The machines are not able to do both real time PCR and multiplexing. The size and fragility of current systems means they are lab based and not able to be used in field conditions.

Current devices for multiplexing require several hundreds of watts to operate and around 75% of this energy goes into the heating and cooling of samples. Such high energy requirements limit the current machines to laboratory based settings where access to a continuous energy supply is available.

Real-time polymerase chain reaction, also called quantitative real time polymerase chain reaction (Q-PCR/qPCR/qrt-PCR) or kinetic polymerase chain reaction (KPCR), is a technique based on PCR, which is used to amplify and simultaneously quantify a targeted nucleic acid molecule. Real Time-PCR enables both detection and quantification. The quantity can be either an absolute number of copies or a relative amount when normalized to DNA input or additional normalizing genes.

The procedure follows the general principle of polymerase chain reaction; its key feature is that the amplified DNA is detected as the reaction progresses in real time. For standard PCR the product of the reaction is detected at its end. Two common methods for detection of products in real-time PCR are: (1) non-specific fluorescent intercalating dyes that disrupt any double-stranded DNA, and (2) sequence-specific nucleic acid probes consisting of oligonucleotides that are labeled with a fluorescent reporter which permits detection only after hybridization of the probe with its complementary nucleic acid target.

The object of the invention is to alleviate some of the problems of the current devices and methods.

SUMMARY

Accordingly, a first aspect of the invention provides a method for adjusting the temperature of a sample comprising the step of heating a substrate with a laser diode light; said light projected on to the substrate to absorb the light and convert the light energy to a heat energy thereby raising the temperature of the substrate corresponding to the intensity of the light energy, the substrate configured to transfer the thermal energy substantially homogenously to the sample.

Another aspect of the invention provides a device for adjusting the temperature of a sample comprising: a laser diode for projecting a light to a substrate; said light adapted to be projected substantially homogeneously on to the substrate to absorb and convert the light energy to heat energy thereby raising the temperature of the substrate corresponding to the intensity of the light energy, the substrate configured to transfer the thermal energy substantially homogenously to the sample.

Another aspect of the invention provides a method for amplifying and/or analyzing a nucleic acid sample comprising the steps of:
a. placing the nucleic acid sample in contact with a substrate;
b. heating the substrate to a first temperature and maintaining the first temperature with a laser diode light source; said light projected on the substrate to absorb the light and convert the light energy to heat energy thereby raising the temperature of the substrate corresponding to the intensity of light energy, the substrate configured to transfer the thermal energy substantially homogenously to the nucleic acid sample;
c. lowering the temperature of the substrate to a second temperature and maintaining the substrate at the second temperature; and
d. detecting a fluorescence signal of the nucleic acid sample.

Other aspects and advantages of the invention will become apparent to those skilled in the art from a review of the ensuing description, which proceeds with reference to the following illustrative drawings of preferred embodiments.

BRIEF DESCRIPTION OF THE DRAWINGS

FIG. 4D: Overall power consumption for the thermal management of the device according to the present invention.

DETAILED DESCRIPTION

Figure 1A:
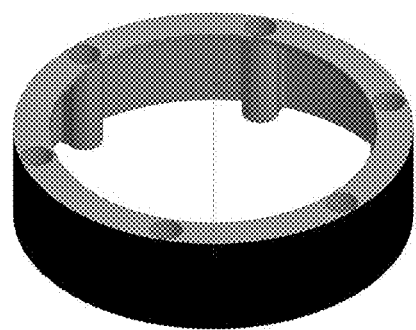
FIG. 1A: Isotopic view of a partially (only outer surface of ring blackened) black substrate according to the present invention.

A method for adjusting the temperature of a sample is described comprising the step of heating a substrate with a laser diode light; said light projected on to the substrate to absorb the light and convert the light energy to a heat energy thereby raising the temperature of the substrate corresponding to the intensity of the light energy, the substrate configured to transfer the thermal energy substantially homogenously to the sample.

Heating the substrate substantially homogenously will ensure that the substrate is heated up quickly using a minimum amount of energy. As the method is designed to be carried out in field conditions where it is difficult to access a large power supply it is necessary to efficiently heat the substrate and thereafter transfer the heat to the sample. Generally the light should be absorbed on the substrate at least at two locations almost simultaneously to allow efficient heating.

There are several embodiments that allow the light to be projected on the substrate. In one category of embodiments, either the substrate or the laser diode are rotated in which case the one souse of light is absorbed resulting in a uniform distribution of thermal energy on the substrate whereby the faster the spinning, the more homogenously the thermal energy distribution is over the substrate surface.

In another category of embodiments two or more laser diode light sources are used to heat the substrate.

In another category of embodiments the method may further comprising the step of optical manipulation of the light by focusing, collimating, splitting, diffracting, switching or reflecting to generate multiple beamlets spatially distributed and directed on to the substrate.

One example of optical manipulation is where the light beam from the laser diode is split, diffracted and/or reflected into at least two beamlet paths allowing the light radiation to project on the substrate at two locations so that the radiated energy is absorbed and converted to heat energy thereby raising the temperature of the substrate corresponding to the radiated light intensity and transfer the thermal energy to the sample.

In another example of optical manipulation light beam from the laser diode light source is optically manipulated to generate plurality of beamlets by splitting, diffracting and reflecting the light beam. These beamlets are spatially directed to a stationary substrate at several locations thereby resulting in a uniform generation of thermal energy on the substrate In another category of embodiments more than one laser diode light sources can be used and optically manipulated to generate plurality of beamlets by splitting, diffracting and reflecting the light beams.

Preferably the method may further comprises the step of removing the light energy from the substrate to lower its temperature and maintain the substrate to a new temperature. This allows the substrate to cool via the ambient air temperature. In one embodiment the cooling of the substrate can be further assisted by actively cooling the substrate with a sprayed mist or a fan or by other methods known in the art.

Preferably the method may further comprise the step of detecting the temperature of the substrate via a sensor not in contact with the substrate. Such a sensor may include a thermopile.

Preferably the method may further comprise the step of detecting a signal from the sample via a sensor. Such a sensor may include a fluorescence detector or a sensor that detects a change in magnetic resonance or any sensor capable of detecting changes in a biological sample.

Preferably the sample is nucleic acid samples. The method and device described can be used for amplification of nucleic acid samples. This has the advantage that it conforms to the traditional workflow. To conform to the traditional workflow in some embodiments the method may further comprise the steps of; cooling the substrate to in turn cool the sample; and detecting the fluorescence of the sample as known in the art.

A device for adjusting the temperature of a sample is described herein comprising: a laser diode for projecting a light to a substrate; said light adapted to be projected substantially homogeneously on to the substrate to absorb and convert the light energy to heat energy thereby raising the temperature of the substrate corresponding to the intensity of the light energy, the substrate configured to transfer the thermal energy substantially homogenously to the sample.

Preferably the device is compact and light weight to allow it to be easily portable and field deployable. The device is designed to use a minimum amount of energy by efficiently heating the substrate. This is achieved by the excitation light being absorbed substantially homogeneously effectively avoiding thermal gradients to conduct a temperature corresponding to the excitation light to the substrate and transferred as heat to the sample. This ensures that the sample is heated up quickly, substantially homogenously and using a minimum amount of energy. As the device is designed to be used in field conditions where it is difficult to access a large power supply it is necessary to efficiently heat the substrate and thereby transfer the heat to the sample.

In one embodiment the substrate that generates thermal energy is external to the sample holder and transfers the thermal energy to the sample by radiation, conduction and convection. In another embodiment the substrate that generates thermal energy holds the sample. In another category of embodiment the substrate that generates thermal energy is suspended within the sample.

In one embodiment a portion of the substrate that comes into contact with the light has high emissivity. In this embodiment preferably the portion of the substrate that comes into contact with the light is black. Surface properties of an opaque substrate are important. Surfaces incident to the laserdiode light should be matte-black for maximum absorption (the emissivity of a black body is 1). However, surfaces not incident to the laser diode light should not be black in order to reduce radiation losses during the heating processes (especially, heating to 95° C. and maintaining 95° during the polymerase hot-start activation and the denaturation step, respectively). Reducing radiation losses at temperatures above ambient temperatures markedly reduces the overall power consumption, as less electrical/optical input power is needed to reach and/or maintain activation, denaturation, and annealing/extension temperatures. Selective (e.g. by masking) black anodization of metals (e.g. aluminum) would be one possible way to generate a matte-black finish. Alternatively, such surfaces might be generated by plating techniques (e.g. 'black gold'). One example to selectively generate a non-black surface would be by physical and/or chemical polishing.

In one embodiment a portion of the substrate that does not come into contact with the light is non-black. Surface properties of the substrate may be important. Matte-black surfaces will radiate much more efficiently than shiny bare metal in the visible spectrum. A shiny metal surface has low effective emissivity due to its low surface area. The emissivity in the visible spectrum is closely related to color. For most materials, the emissivity in the visible spectrum is similar to the emissivity in the infrared spectrum. Preferably, the surface of the substrate that comes into contact with the excitation light is black to maximize thermal transfer from the substrate to the sample, however, the portions of the substrate that do not come into contact with the excitation light are preferably white or shiny bare metal to avoid unnecessary heat loss from the device.

Preferably the substrate is made of a material with low density, low specific heat capacity, high thermal conductivity or high absorption coefficient. A low (thermal) mass enables fast temperature transition rates/changes. Furthermore, a low thermal mass correlates with a low heat capacity, thus keeping the overall power consumption for heating and cooling at a minimum. Moreover, high thermal conductivity provides an efficient heat transfer, prevents the buildup of temperature gradients, and thus allows for a uniform temperature distribution within the substrate. In addition, the temperature uniformity can be further enhanced by rotating the substrate relative to the beamlets. Also, this rotation allows analyzing multiple qPCR samples by moving them past a miniaturized fluorescence detector. All components in physical contact with the substrate, except the sample and/or sample tubes, should be thermal isolators with low/poor heat capacities.

The substrate may be made of the following types of materials: metals, metal alloys, and metal composites (e.g., aluminum, magnesium, and steel), ceramics (e.g. aluminum nitride), thermally conductive polymers (e.g. polypropylene, polycarbonate, polyamides, polyolefin, and liquid crystal polymers), diverse carbon species (e.g. diamond, carbon nanotubes, and carbon fibers/particles), and any combinations thereof (e.g. a gold coated thermally conductive polymer).

In one embodiment the substrate is in the form of a band such as a ring. This may take on several forms for example the entire outer surface of the ring may be made matte-black by selective anodic oxidation of a polished aluminum ring using diverse masking techniques (e.g. wax) (see FIG. 1A). In this example, the height of the ring correlates with the diameter of the laserdiode light beamlets. Additionally, the holes/slots for accommodating the PCR tubes might be blackened or not.

Figure 1B:
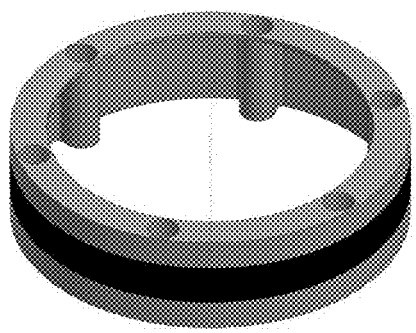
FIG. 1B: Isotopic view of a partially (black band on outer surface of the ring) black substrate according to the present invention.

In yet another embodiment the substrate is in the shape of the ring, whereby only a small matte-black band covers the outer surface of the ring (see FIG. 1B). This set-up has a smaller matte-black surface area and thus reduced radiation losses and a lower overall power consumption. Here, the diameter of the laserdiode light beamlets can be varied by using different types of collimators/focusers (typically 0.5-5 mm beam diameters over a free-space traveling distance of 30-200 mm of the laserdiode light). Additionally, the holes/slots for accommodating the PCR tubes might be blackened or not.

Figure 1C:
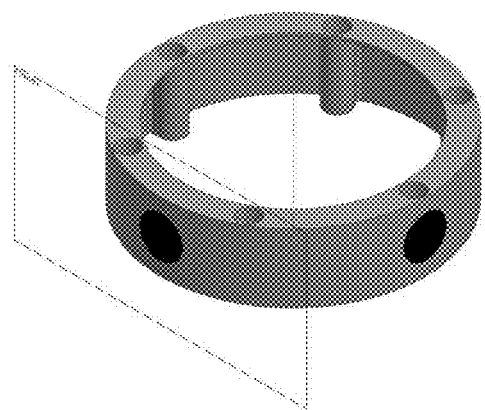
FIG. 1C: Isotopic view of a partially (black circles on outer surface of the ring) black substrate according to the present invention.

In yet another embodiment the substrate is in the shape of the ring, whereby only a few matte-black circles cover the outer surface of the ring (see FIG. 1C). In terms of electrical/optical input power, this set-up represents one of the most economic solutions and does not require the substrate being rotated.

Figure 1D:
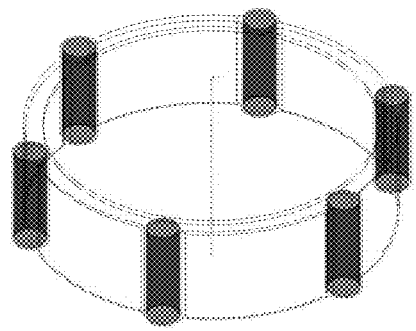
FIG. 1D: Isotopic view of a partially (black slots/holes that accommodate the sample) black substrate according to the present invention. Alternatively, the entire substrate is transparent and only the PCR sample tubes are black.

In yet another embodiment the substrate is in the shape of a transparent ring, whereby only the holes/slots accommodating the PCR tubes are blackened (see FIG. 1D).

In one embodiment the substrate may be formed of a foam. For example a metallic foam In one embodiment the substrate may be in the form of particles within the sample. For example in acolloidal arrangement with particles or photosensitizer within the PCR sample (see FIG. 1E). The particles within the sample might be in the form of a solution, suspension, (colloidal) dispersion, or an emulsion. Examples for such substrates might be [but not limited to] quantum dots (e.g. gold particles), magnetic particles, synthetic diamonds, photosensitizers, and any combinations thereof. Besides their role as a substrate, quantum dots, magnetic particles, and photosensitizers could be employed as probes for additional sensing purposes (e.g. a spectral shift in the emission spectrum of a quantum dot could be used as a temperature sensor). Also, a magnetic particle (e.g. silica-coated paramagnetic particles) could be used for a sample preparation preceding the PCR.

It is also possible to use the substrate directly as a disposable reaction vessel. FIG. 1F shows an illustrative example of a substrate, which is manufactured by co-injection molding of a matte-black thermally conductive polymer (e.g. polypropylene) and a native transparent polypropylene. Here, the transparent bottom or lid will enable optical detection. Besides being low-cost, a disposable substrate also prevents cross-contamination between subsequent qPCR runs—an important aspect in clinical diagnosis of infectious diseases.

Figure 2A:
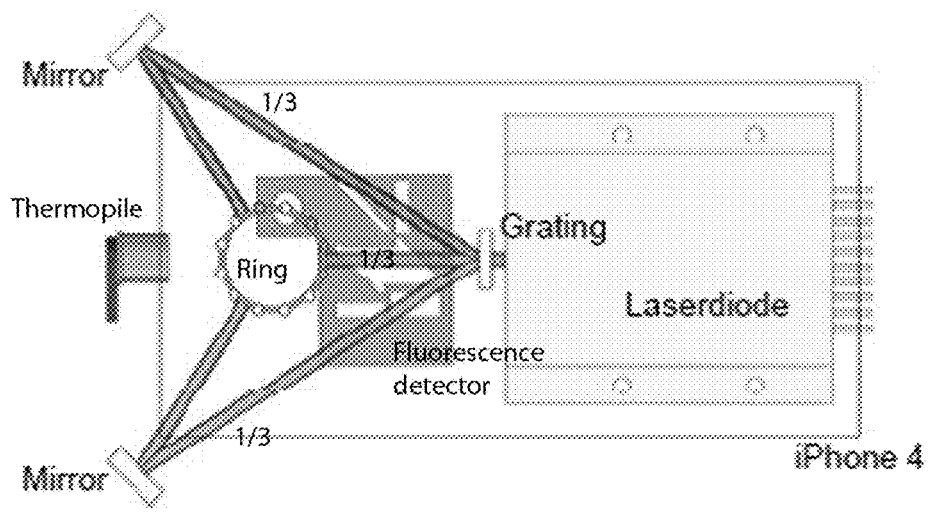
FIG. 2A: Top view of a set-up that utilized a JOLD-4.2-BAXH-1E laserdiode from Jenoptik with built-in optical components for beam shaping/collimation. In this particular example, a 1×3 diffractive beamsplitter (2D grating) is used to evenly split the beam into three beamlets.
Figure 2B:
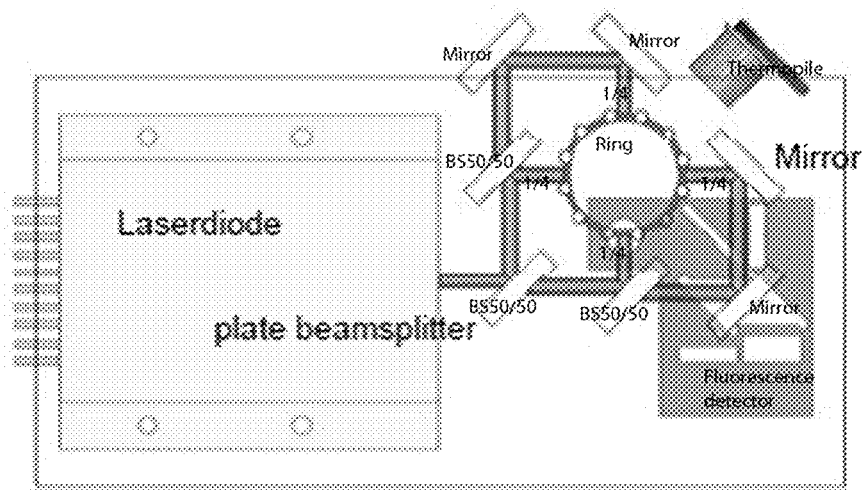
FIG. 2B: Top view of a set-up that utilized a JOLD-4.2-BAXH-1E laserdiode from Jenoptik with built-in optical components for beam shaping/collimation. In this particular example, 4 beamsplitters (50% transmission and reflection each) are used to evenly split the beam into 4 beamlets.

In yet another embodiment the substrate may be in the form of a metal mesh or metal foam within the PCR sample solution The device includes a laserdiode light source. In one embodiment the device further includes an additional laserdiode light source. Two or more laserdiodes can be operated at different wavelengths, frequencies, phases, or optical output powers. Laserdiode light is also referred to herein as beam(s) or beamlet(s). For routing the laserdiode light to the substrate, different optical components, such as collimators/focusers, beamsplitters (e.g. plate beamsplitters), optical switches, diffractive optics (e.g. 2D gratings or diffusers), mirrors, etc. can be used. One or all of these optical elements can already be an integral part of a laserdiode. One such example would be a laserdiode with an in-built Fresnel lens for beam shaping/collimation (see FIGS. 2A and 2B). In one embodiment, a beam shaped in the form of an annular ring (e.g. generated by an axicon) can be used, whereby the laserdiode light might be projected from either above or below the substrate. This set-up would have the advantage, that one optical element alone would be sufficient to provide a substantially homogeneous illumination of the substrate without the build-up of local temperature gradients.

In one embodiment the device further comprises one or more optical elements selected from a beam splitter, a diffractive optical element, a mirror, a lens, a light guide or an optical switch is positioned in the path of a light beam between the laser diode and the substrate. There are several formats to optimize the use of optical elements. Any permutations of laser diodes and optical elements should be calculated to heat the substrate substantially uniformly.

Figures 3A, 3B:
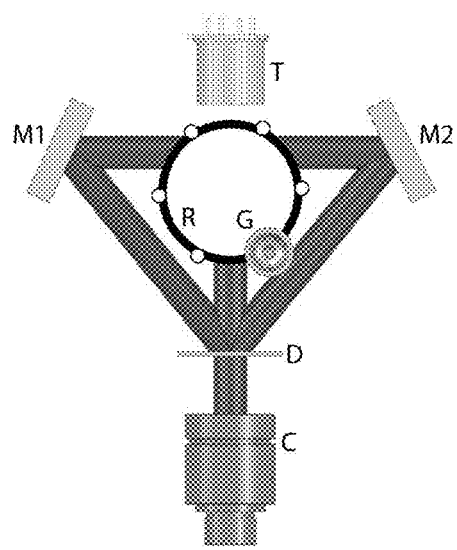
FIG. 3A: Top view of a set-up that utilized a 1×3 diffractive optical element (DOE) for beamshaping according to the present invention.
FIG. 3B. Temperature uniformity at 60° C. for various beamshaping configurations. All setups resulted in temperature uniformities of less than ±0.5° C. Centrosymmetric arrangements with more than three beamlets achieve temperature uniformities of less than ±1° C. Fiberoptics, diffractive optical elements (DOEs), and beamsplitters were used for beamshaping.

In one embodiment the device comprises a 1×3 diffractive optical element (DOE) (as an example of a two-dimensional grating to manipulate laserdiode light) in combination with two mirrors (see FIG. 3A). Here, the beam of a fiber-pigtailed laserdiode is collimated and split into 3 beamlets of equal intensity (1:1:1), which are equally spaced (120°) along the ring. The beamlet of the 0st order impinges directly upon the ring, whereas the beamlets of the 1st orders are deflected onto the ring by two mirrors. This particular set-up provides a uniform temperature distribution within a stationary (non-rotating) ring. A thermopile temperature sensor in a closed loop is employed for contactless temperature measurements. Various diffraction orders might be used. Also, three-dimensional diffractive optical elements might be employed. Preferably, the split ratio of the beamlets should be equal. However, any split ratios can be employed. Although non-equal split ratios might result in a larger temperature gradient within the ring, the temperature gradient can be easily lowered under ±0.5° C. by varying the rotational velocity of the ring. For any given setup, the temperature uniformity can be effectively controlled within ±0.5° C. by adjusting four independent parameters: the relative orientation, number, and optical output power of the beamlets, as well as the rotational speed of the ring. Increasing the rotational speed of the ring compensates for an imbalanced power distribution in the beamlets—a feature, which opens up new ways for dispensing the infrared (IR) radiation to the ring (see FIG. 3B). Legend for FIG. 3A: C collimator, D 1×3 diffractive optical element (DOE), G glass PCR tube, M1 and M2 mirrors to project split beamlets onto ring, R ring, T thermopile. The design of the ring shown in FIG. 3A is advantageous as it provides a very low thermal mass for a given ring diameter.

Figure 3C:
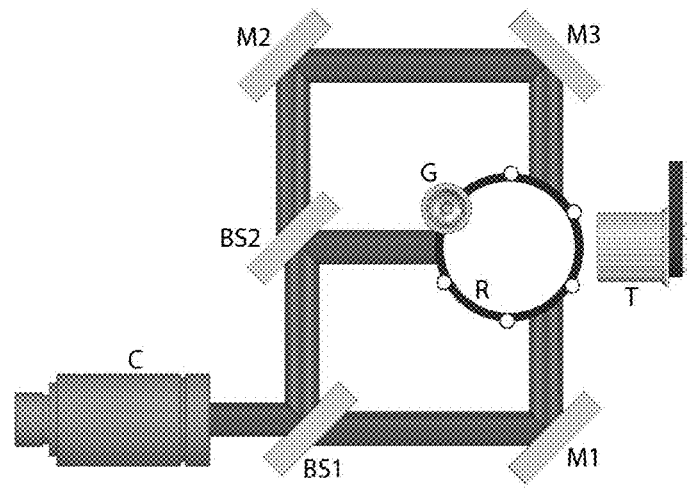
FIG. 3C: Top view of a set-up that utilized a two beamsplitters and three mirrors to generate three beamlets of equal intensity (1:1:1) according to the present invention.
Figure 3D:
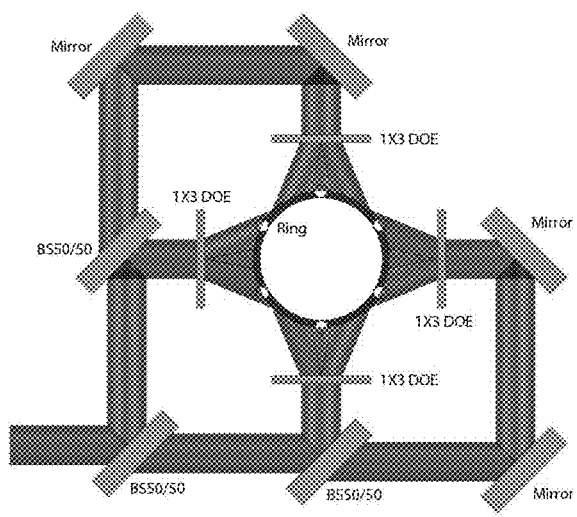
FIG. 3D: Top view of a set-up that utilized a combination of beamsplitters and diffractive optical elements to generate 12 beamlets of equal intensity (1:1:1:1:1:1:1:1:1:1:1:1) according to the present invention.

In yet another embodiment the device comprises an array of 2 plate beamsplitters in combination with three mirrors (see FIG. 3C). Here, the beam of a fiber-pigtailed laserdiode is collimated and split into 3 beamlets of equal intensity (1:1:1), which are equally spaced (120°) along the ring. This particular set-up provides a uniform temperature distribution within a stationary (non-rotating) ring. A thermopile temperature sensor in a closed loop is employed for contactless temperature measurements. The number of beamsplitters and mirrors might be varied. Preferably, any combination/permutation involving arrayed beamsplitters should result in beamlets of equal intensity. However, although non-equal split ratios might result in a larger temperature gradient within the ring, the temperature gradient can be easily adjusted by varying the rotational velocity of the ring. Alternatively, a 1×N fiberoptic beamsplitters can be used (see FIG. 3D).

In yet another embodiment the device comprises a combination of 4 arrayed beamsplitters, four mirrors, and 4 1×3 diffractive optical elements (see FIG. 3E) Here, the beam of a fiber-pigtailed laserdiode is collimated and split into 12 beamlets of equal intensity (1:1:1:1:1:1:1:1:1:1:1:1), which are equally spaced (30°) along the ring. This particular set-up provides a uniform temperature distribution within a stationary (non-rotating) ring. A thermopile temperature sensor in a closed loop is employed for contactless temperature measurements. Alternatively, a diffuser might be used instead of 1×3 diffractive optical element. The number of beamsplitters, mirrors, and diffractive optical elements might be varied. Preferably, any combination/permutation involving arrayed beamsplitters should result in beamlets of equal intensity. However, although non-equal split ratios might result in a larger temperature gradient within the ring, the temperature gradient can be easily adjusted by varying the rotational velocity of the ring.

Preferably the device may further comprise a fan or a blower to remove thermal energy from the substrate A fan or a blower may actively vary or control the temperature of the substrate (including PCR tubes and PCR samples). Alternatively, a vortex tube or compressed air might be used.

Preferably the device may further comprise a signal processor for detecting a signal of the sample being analyzed. The device sensor may be a fluorescent signal processor connected to a fluorescence detector for processing a fluorescent signal (emerging from the PCR sample in the PCR tube). Alternatively it could be for the detection of electro Preferably the device comprises a portable battery. The laser diode light source used to heat the substrate requires electrical energy for operation. The device is designed to consume less than 10 Wh of electrical energy to generate the thermal cycles for denaturation, annealing and extension. Thus the device will be compact and light weight which allows it to be easily portable and field deployable. The device can be used in remote settings and powered by Lithium ion batteries comparable to those used in laptops and notebook computers. The device preferably comprises a small form-factor battery (lithium-ion or lithium polymer-based batteries).

Figure 6A:
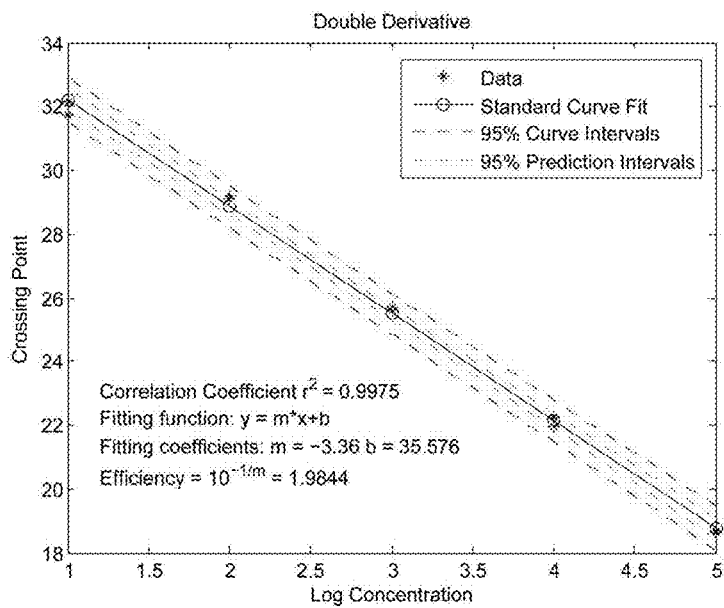
FIG. 6A: Standard curve for avian influenza H5.
Figure 6B:
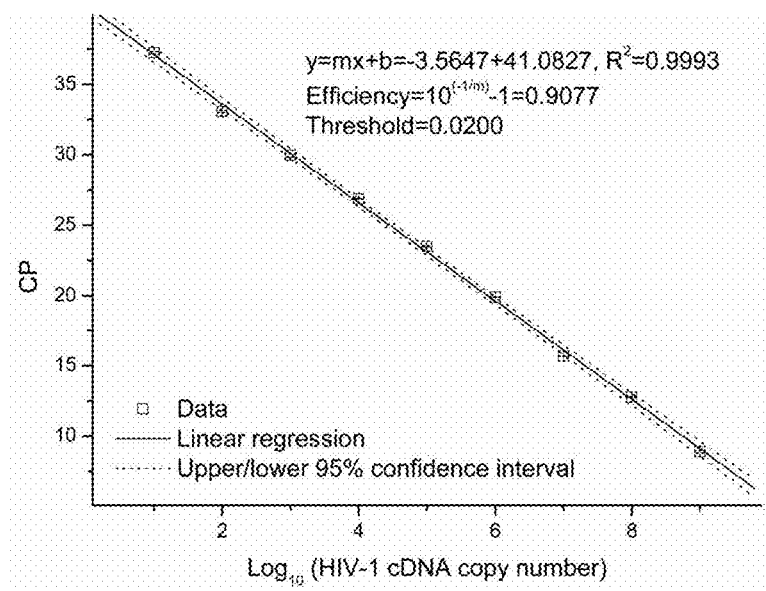
FIG. 6B: Standard curve for HIV-1.
Figure 6C:
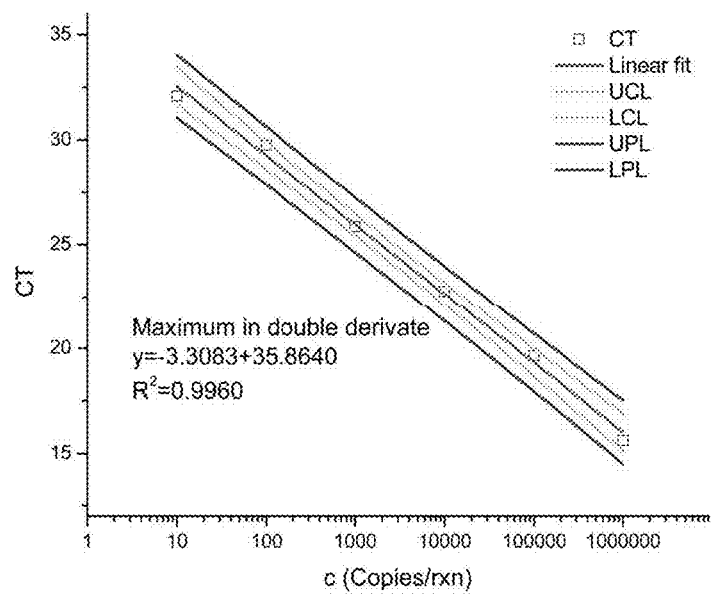
FIG. 6C: Standard curve for tuberculosis (TB).
Figure 10A:
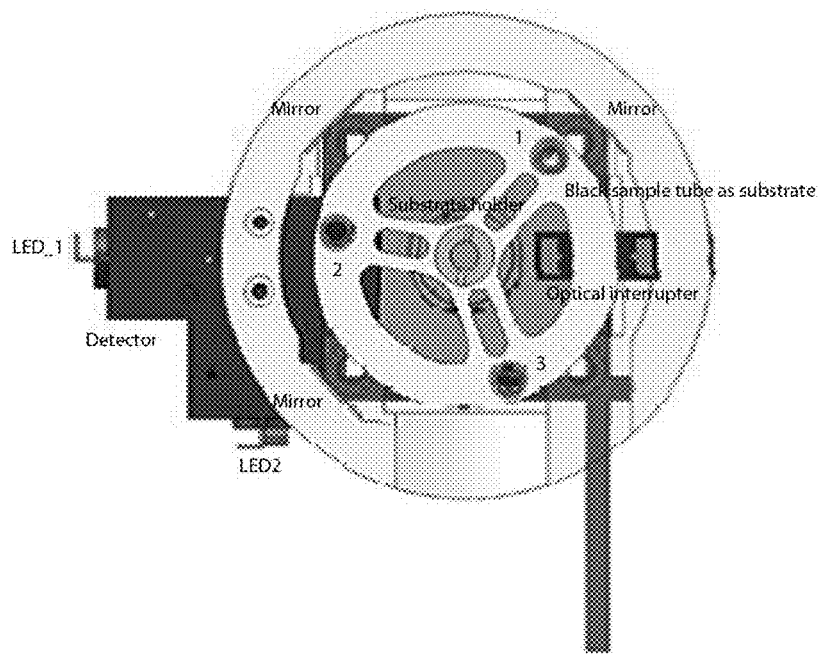
FIG. 10A: Top view of one device according to the present invention.
Figure 10B:
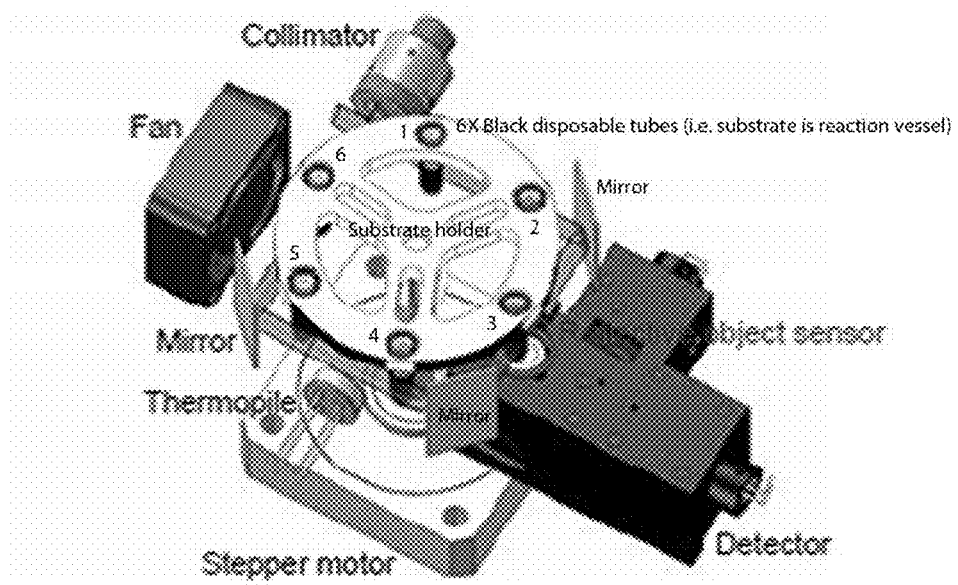
FIG. 10B: Isotopic view of one device according to the present invention.
Figure 10C:
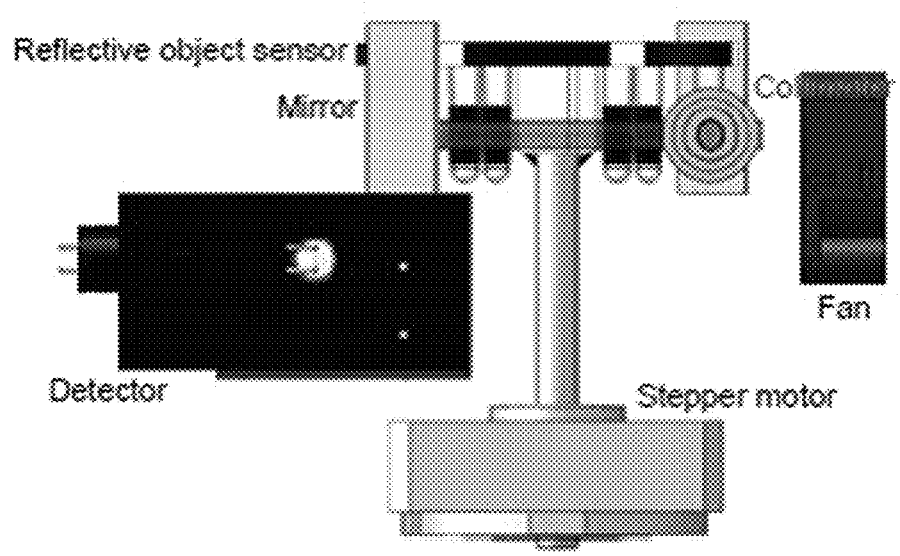
FIG. 10C: Side view of one device according to the present invention.

In one embodiment the substrate may comprise two or more substrates. This possibility is to use one collimated laserdiode light beam (without placing any other optical elements except at least one mirror between the collimator and the substrate) to project the laserdiode light at multiple substrates (see FIG. 10A-C). This is an advantage, because only a limited number of optical elements would be needed to affect heating. A further advantage of this set-up is, that the thermal mass of the samples is more or less identical with the thermal mass of the substrates, which would enable faster heating and cooling (compared to one large substrate with a rather large thermal mass). Also, the substrates would act as disposable reaction containers. E.g. in FIG. 10A, 3 rotating disposable black substrates, which are slotted into a substrate holder, are heated simultaneously by one laserdiode light beam. E.g. in FIG. 10B, 6 rotating disposable black substrates, which are slotted into a substrate holder, are heated simultaneously by one laserdiode light beam.

Figure 11:
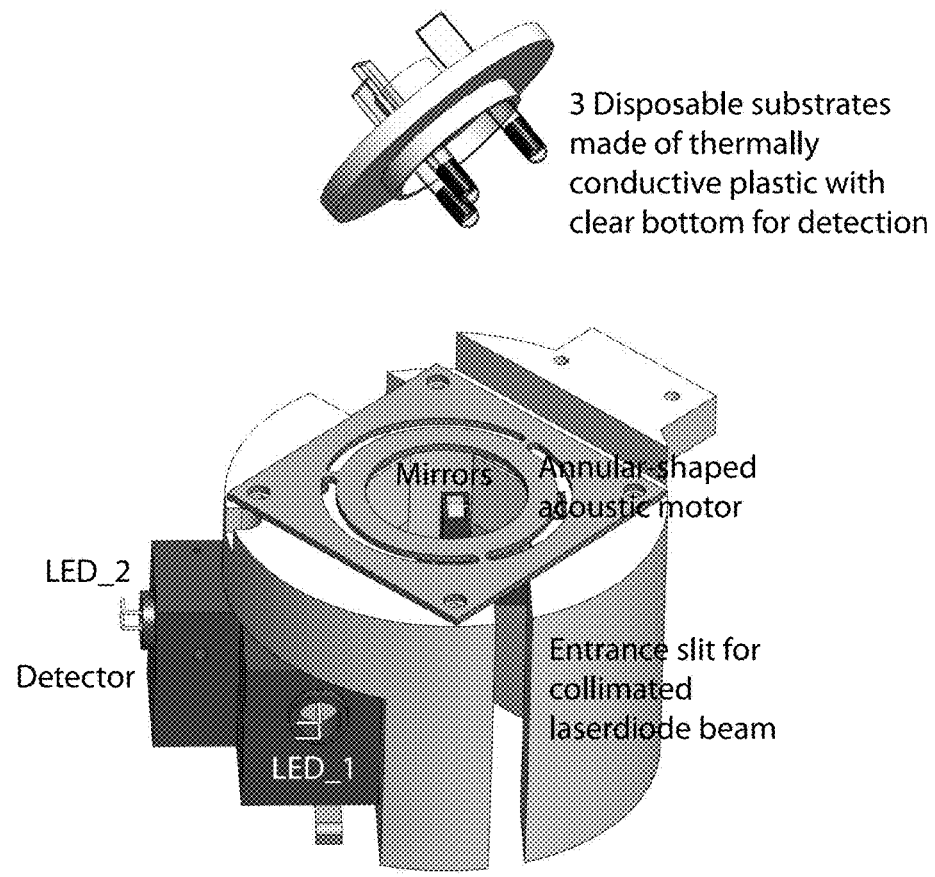
FIG. 11: Side view of one device according to the present invention.

Instead of a stepper motor, a DC motor or acoustic motors (see FIG. 11) might be used. FIG. 11 shows an example of a printed circuit board (PCB)-based motor, which uses friction force to rotate the substrate holder. In total 3 black disposable substrates are slotted into the substrate holder, whereby the laserdiode beam is guided as outlined in FIG. 10A.

The device may further comprise a temperature sensor not in contact with the substrate.

The compact size and the low weight of the device make it ideally suited for portability. Among those temperature sensor might be Pt RTD temperature sensors, thermocouples, and non-contact thermal and optical sensors, such as thermopiles, bolometers, or pyrometers.

A method for amplifying and/or analyzing a nucleic acid sample is described herein comprising the steps of:

a. placing the nucleic acid sample in contact with a substrate;
b. heating the substrate to a first temperature and maintaining the first temperature with a laser diode light source; said light projected on the substrate to absorb the light and convert the light energy to heat energy thereby raising the temperature of the substrate corresponding to the intensity of light energy, the substrate configured to transfer the thermal energy substantially homogenously to the nucleic acid sample;
c. lowering the temperature of the substrate to a second temperature and maintaining the substrate at the second temperature; and
d. detecting a fluorescence signal of the nucleic acid sample.

Preferably more than one nucleic acid sample is amplified.

Preferably the thermal cycle comprises real time polymerase chain reaction to amplify the nucleic acid sample. A detailed method may include the following steps.

a. associating the nucleic acid sample with the substrate for transfer of thermal energy;
b. heating the substrate with electromagnetic radiation from a laser diode light source, the substrate configured to absorb the radiation and convert the radiated energy to heat energy thus raising the temperature of the substrate corresponding to the radiated light intensity; and then transfer the heat energy to the nucleic acid sample,
c. a cooling system such as a fan or a blower to remove thermal energy from the substrate; and then maintaining the temperature of the substrate at this new thermal state by heating the substrate with a lower light intensity from the laser diode;
d. one thermal cycle consists of a heating and cooling/maintaining phase
e. thus producing a thermal cycle comprising of at least one heating and cooling cycle and the nucleic acid sample containing at least one nucleic acid which undergoes amplification in response to the thermal cycle;
f. detecting the fluorescence of the nucleic acid sample.

The method is suitable for amplifying more than one nucleic acid sample.

Preferably the method comprises real time polymerase chain reaction to amplify the nucleic acid sample.

The method relies on photonic principles, whereby an excitation light converts the light energy to thermal energy and transfers the thermal energy to a sample.

Preferably the method is for amplification of more than one nucleic acid sample. Preferably the method uses real time polymerase chain reaction to amplify the nucleic acid sample. It would be understood that the method described herein may be applied to any nucleic acid amplification methods known in the art.

Preferred Embodiments

The system is able to capture real-time qPCR data using a multiplex-capable fluorescence detector. Presently, up to 4 colors/optical channels (blue, green, orange, and red) in the visible range of the spectrum (VIS) can be addressed simultaneously by placing one or more detectors along the ring perimeter. However, the system is not limited to 4 optical channels and can be upgraded accordingly, e.g. by introducing additional channels in the ultraviolet (UV), VIS, and near infrared range (NIR). Dependent on the systems' configuration, 1-36 samples can be processed at a time. Typically, the working volumes are in the range of 1 to 10 uL. If needed, larger volumes can be processed by changing the system accordingly.

The systems' mode of operation completely relies on photonic principles: light at different wavelengths, frequencies, and phases is used for heating/cooling, temperature sensing, positional sensing, and optical detection.

Figure 4A:
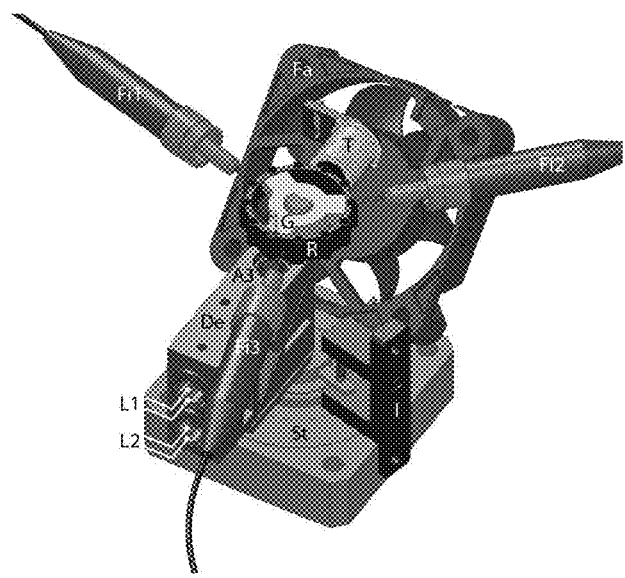
FIG. 4A: Isotopic view of a thermocycler device that utilized a 1×3 fiberoptical beamsplitter for uniformly heating the ring according to the present invention.

FIG. 4A depicts an example of a set-up. An 8 W 808 nm-laserdiode light beam is equally split into 3 beamlets using a 1×3 fiberoptic beamsplitter and projected onto a stepper motor-driven matte-black ring holding multiple PCR sample tubes. A thermopile temperature sensor working above 5 µm in a feedback loop controls the ring temperature by regulating the laserdiode drive current. In addition to natural convection and/or radiation, a fan allows for active cooling using ambient air. An optical interrupter/flag operating at 980 nm moves the black ring—and thus PCR sample tube 1 to its home position above an optical detection system for initiating the real-time fluorescence data acquisition, which is performed by means of incremental step counting in either a stop-and-go or on-the-fly mode. Two-color optical detection (FIG. 5A) is monitored between 475 and 655 nm. Legend for FIG. 4A: A3 aspheric lens of the fluorescence detection system, De two-color optical detection system, Fa cooling fan for active cooling with ambient air, Fil-3 3 fiberoptic ends of a 1×3 fiberoptic beamsplitter, G PCR glass capillary, I optical interrupter together with optical flag for indexing/mapping of the sample positions, L1 and L2 LEDs used as excitation lightsources in the fluorescence detector, R black ring for absorbing the laserdiode light guided by the fiberoptics, St stepper motor to rotate the ring, T thermopile temperature sensor for controlling the ring temperature, W wheel for coupling the ring to the motor shaft. The bar size is 10 mm. The interrupter might be replaced by an absolute or incremental encoder.

Figure 4B:
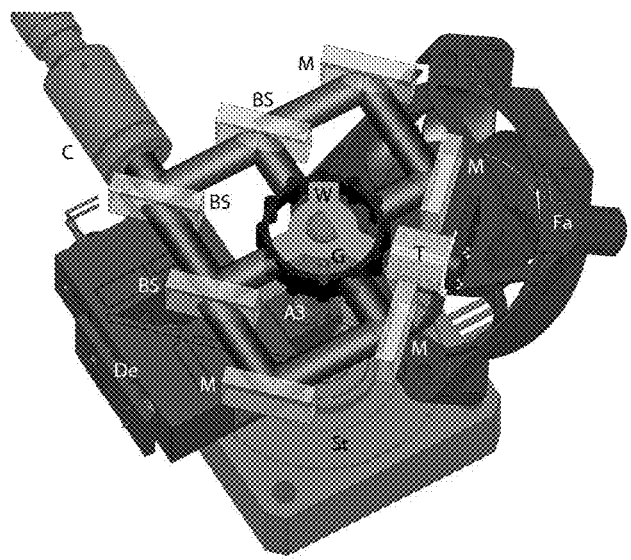
FIG. 4B: Isotopic view of a thermocycler device that utilized arrayed beamsplitters for uniformly heating the ring according to the present invention.

FIG. 4B depicts yet another set-up, in which a collimated light beam of a 10 W 980 nm-laserdiode is collimated, equally (1:1:1:1) split into 4 beamlets using an array of plate beamsplitters and mirrors and projected onto a stepper motor-driven matte-black ring holding multiple PCR sample tubes. The split ratio of all three beamsplitters is 50:50 (transmission/reflection), i.e. all 4 beamlets impinging on the black ring carry 25% of the original intensity. Legend for FIG. 4B: A3 aspheric lens of the fluorescence detection system, BS 50:50 plate beamsplitter, C fiberpigtailed collimator for collimating or focusing the laserdiode light, De two-color optical detection system, Fa cooling fan for active cooling with ambient air, G PCR glass capillary, M 45°-mirror to project the beamlets onto the ring, R black ring for absorbing the laserdiode light guided by the fiberoptics, St stepper motor to rotate the ring, T thermopile temperature sensor for controlling the ring temperature, W wheel for coupling the ring to the motor shaft. It is understood that other types of optical arrangements might be used instead, e.g. a monolithic approach, in which beamspliters and mirrors are fused into one optical element. Also, beamsplitters with different split ratios, coatings, and incident angles might be combined. Moreover, mirrors having different coatings and incident angles might be combined. Using various permutations, the thermal management of the device might be accomplished with laserdiodes operating at different wavelengths and/or intensities.

Figure 4C:
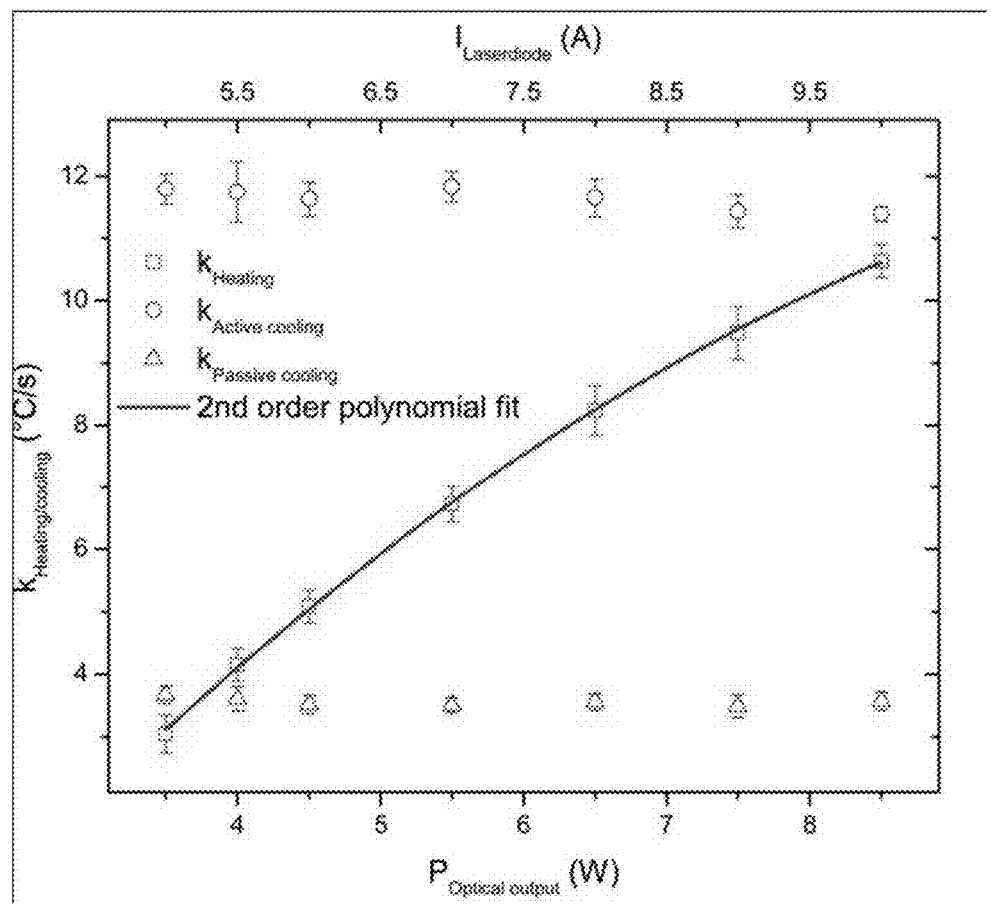
FIG. 4C: Heating as well as active and passive cooling rates for the ring according to the present invention.

A matte-black black anodized aluminum ring is used as the substrate holder to absorb infrared radiation from the beamlets (see FIGS. 1A-E). The absorbed heat is transferred by conduction and/or radiation to the PCR sample tubes held at locations around the substrate holder. The combination of a black anodized aluminum ring in combination with polypropylene (PP)-overmolded glass or plastic PCR sample tube, and polyether ether ketone (PEEK) wheel yields temperature transition rates of more than ±10° C./s (see FIG. 4C) and an average power consumption of around 4 W (see FIG. 4D). Besides aluminum, other thermally conductive materials, such as metals, metal alloys, and metal composites, ceramics, thermally conductive polymers, diverse carbon species, and any combinations thereof can be used. Due to its low specific weight matte-black anodized magnesium is preferable.

In one embodiment, the entire ring is matte-black. A matte-black surface can be generated by various techniques, such as anodization methods, electrochemical plating, electroless deposition, spray painting, carbonization, incorporation of carbon fibers, incorporation of photosensitizers, etc. A matte-black surface is preferred because it acts like a black body, thereby absorbing all incident electromagnetic radiation over a wide wavelength range.

In another embodiment, the ring surface has an emissivity value of larger than 0.9. In yet another embodiment, only those segments of the ring, on which the infrared (IR) radiation impinges, are blackened (e.g. with a coating having an emissivity value of larger than 0.9). In yet another preferred embodiment, the ring coating has an emissivity value substantially equals to 1. The other portions are not blackened or coated in order to minimize radiation losses, which might contribute as much as 30%. Preferable those non-blackened portions should have an emissivity of less than 0.9 (see FIGS. 1A-E). In addition to IR, other wavelengths of the electromagnetic spectrum, such as ultraviolet (UV) or visible (VIS) can be utilized.

Figure 5A:
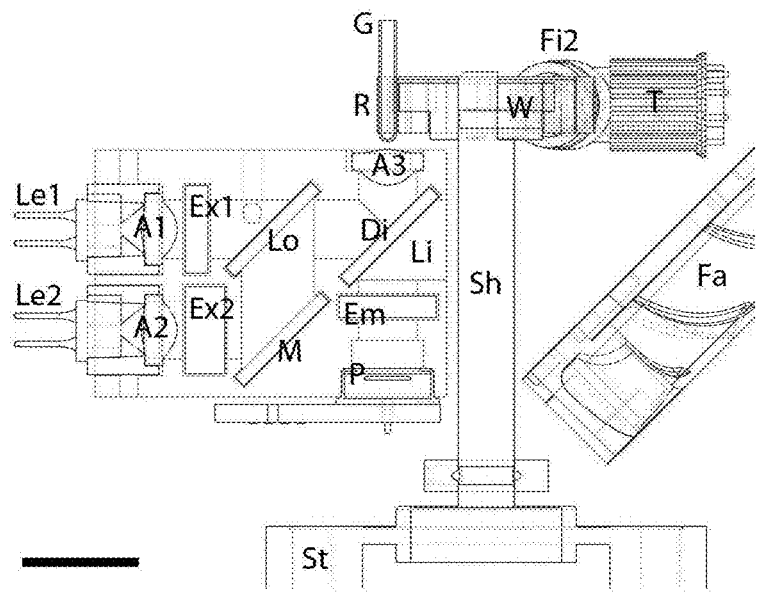
FIG. 5A: Side view of a dual-channel fluorescence detector employed in the device.
Figure 5B:
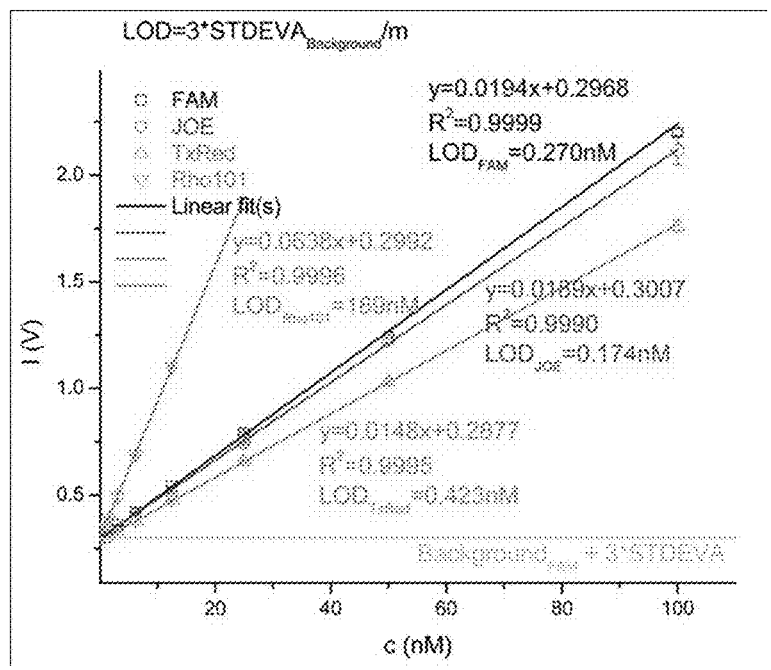
FIG. 5B: Limits of detection (LODs) for the fluorescence detectors used for this device.

The two-channel fluorescence detector is based on a miniature optical bench populated with common (electro) optical components (see FIG. 5A). Utilizing low-cost LEDs, antireflective (AR)-coated aspheric lenses, a hermetically-sealed silicon (Si) photodiode, as well as hardcoated filters does not require any maintenance or calibration during the entire lifecycle of the device. Unlike to an off-axis orientation, the in-axis configuration of the exciation and emission beam pathways adds more flexibility with respect to the PCR sample tube position and geometry. Moreover, each LED is individually modulated, which makes it possible to simultaneously monitor both optical channels under ambient light. FIG. 5A shows a side view of two-color optical detection system. Legend for FIG. 5A: A1 and A2 aspheric lenses for collimating LED excitation light, A3 aspheric lens for focusing excitation light into the PCR sample tubes and collimating fluorescence light from the PCR sample tubes onto the photodetector (see FIGS. 4A and B), Di dualband dichroic mirror, Em dualband emission filter, Exl and Ext excitation filters, Fa fan for active cooling with ambient air, Fil-3 1×3 fiberoptic beamsplitter adapters, G glass PCR tube, Li lighttrap for minimizing stray light being backscattered from the dicroic mirror, Lo longpass filter, P Si photodiode, R matte-black ring, Sh stepper motor shaft, St stepper motor, T thermopile temperature sensor, W wheel for coupling the ring to the stepper motor shaft. Bar size is 10 mm. In another embodiment, a bolometer or pyrometer might be used for temperature control. Despite employing only standard microscopy fluorescence filter sets and using less than 5 µL qPCR reaction volumes, the device rivals any thermocycler in the market with limits of detection (LODs) of less than 1 nM for most fluorogenic probes popular in qPCR (see FIG. 5B).

So far, the system has been evaluated with clinical samples using World Health Organisation standards in qPCR applications targeting infectious diseases, such as influenza (see FIG. 6A), HIV-1 (see FIG. 6B), tuberculosis (see FIG. 6C), and hepatitis (data not shown). We have run feasability studies with blood samples using the smart amplification process (SMAP) aiming at companion diagnostics, for example warfarin (data not shown). Unlike PCR, SMAP is an isothermal amplification process performed at 60° C., in which the denaturation step is enzymatically effected. Consequently, only around 1.4 W average power consumption is required, which is why isothermal amplification formats are an attractive choice for decentralized diagnostic tests using our device.

Laserdiodes used so far ranged from under 400 nm (UV) to more than 2300 nm.

Figure 7A:
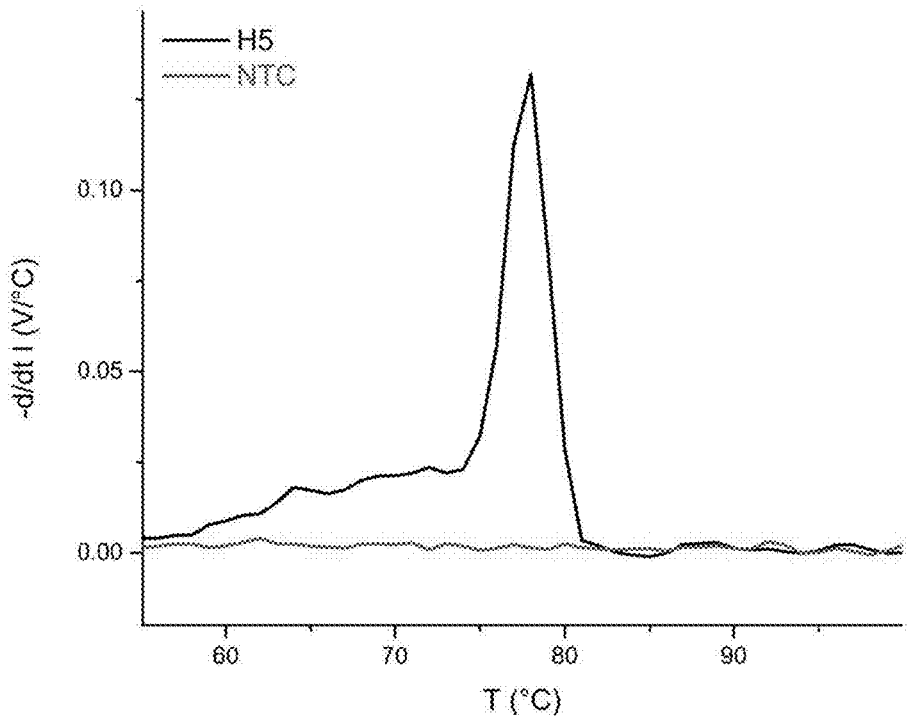
FIG. 7A: Melt curve analysis (MCA) for avian influenza H5 as target.

FIG. 7A depics a melt curve analysis for the H5 target (black) and a no-template control (red).

The low power consumption combined with a weight of less than 2 kg and small DIN A5-form factor make it possible to run the device with a standard Li-ion 12-cell 98 Wh laptop battery for a whole working day in the field.

In a further embodiment, the device/system contains additional components, such as a display, global positioning system (GPS), battery/recharging circuit, wireless local area network (WLAN), interlock system(s) to protect the user from radiation hazards during operation, a beam shutter, absolute or incremental position encoders, MCU/embedded PC, controller(s), and software for each of those; and a power source for powering said device.

Figure 8A:
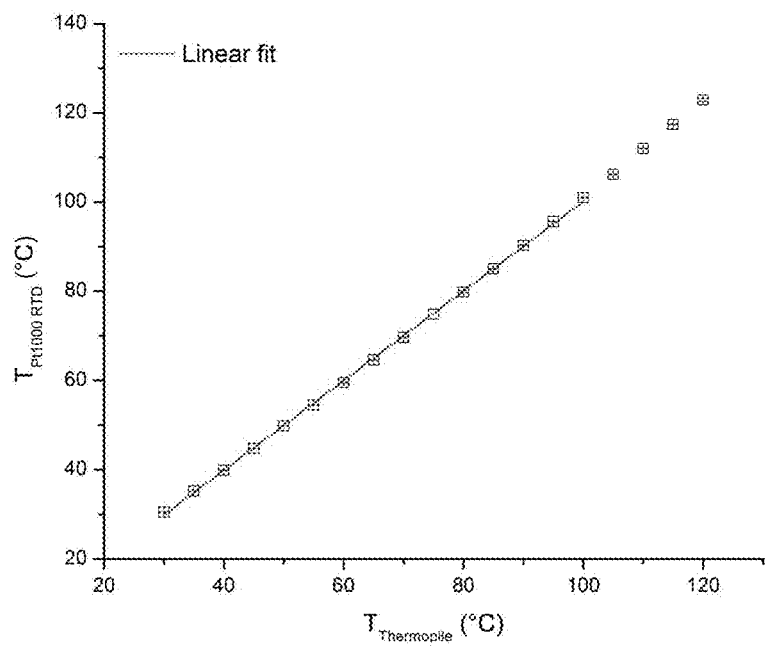
FIG. 8A: PCR sample temperature measured by a Pt1000 RTD temperature sensor versus ring temperature monitored by a thermopile.

FIG. 8A shows the correlation of the qPCR sample temperature measured by a Pt1000 resistive temperature device (RTD) sensor and a thermopile, which was calibrated for temperatures between room temperature and 100° C.

Figure 8B:
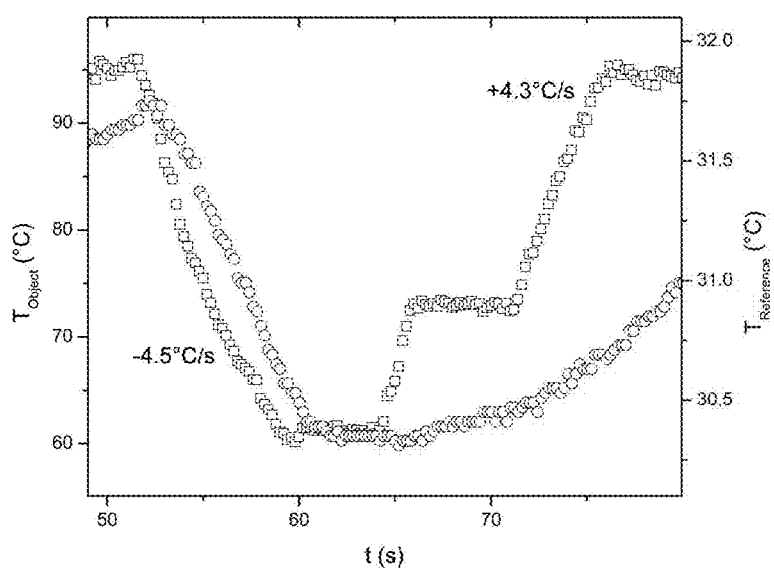
FIG. 8B: One PCR thermocycle (5 s each at 95° C., 60° C., and 72° C., respectively) monitored in closed loop by a thermopile according to the present invention.

FIG. 8B depicts one full thermocycle (5 s at 95° C., 5 s at 60° C., and 5 s at 72° C.), whereby the temperature was monitored using a thermopile. Black indicates the object temperature and blue the reference temperature within the thermopile.

Figure 8C:
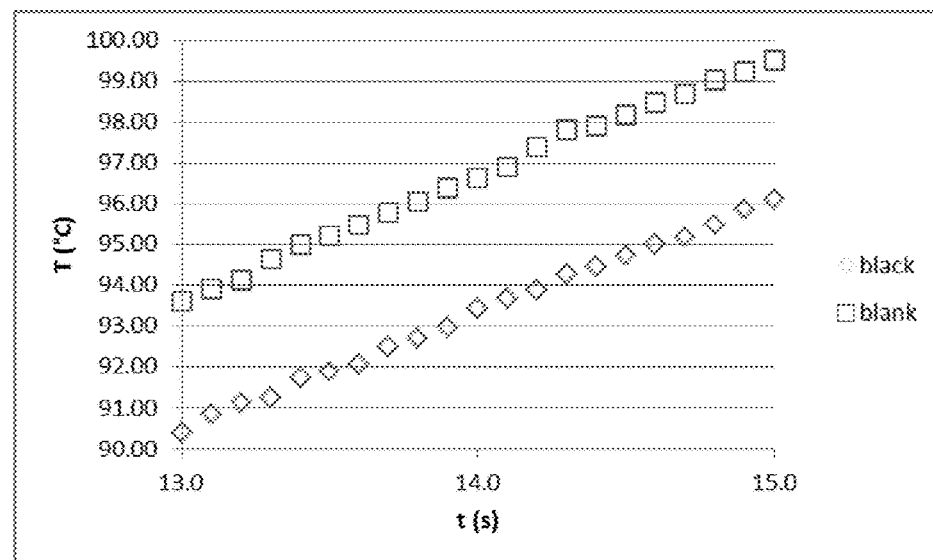
FIG. 8C: Based on the same input optical power, a partially blackened ring reaches 96° C. (denaturation temperature) faster. 'Blank' means that the inside of the ring is bare polished aluminum metal.

The comparison of an entirely black ring and a partially black ring (see FIG. 8C) demonstrates, that radiation losses are lowered by using a partially blackened ring (inside and holes/slots have been protected during the black anodization process). Here, the partially blackened ring reaches 95° C. in a shorter time (see FIG. 8C).

Figure 1E:
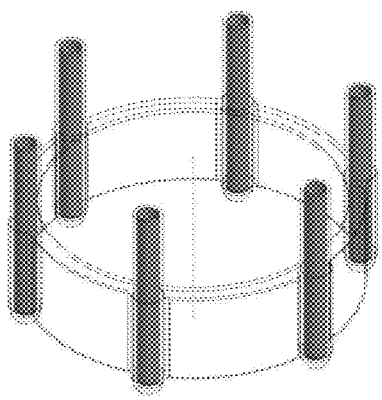
FIG. 1E: Isotopic view of a transparent substrate holding PCR tubes with PCR samples, whereby the PCR samples contain a black substrate according to the present invention. Alternatively, the black substrate might be adsorbed to the PCR sample tubes.
Figure 1F:
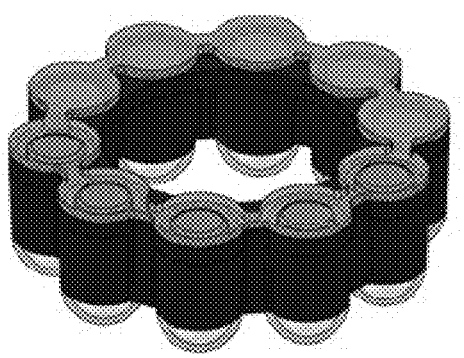
FIG. 1F: Reactions vessel as disposable substrate according to the present invention.
Figure 9:
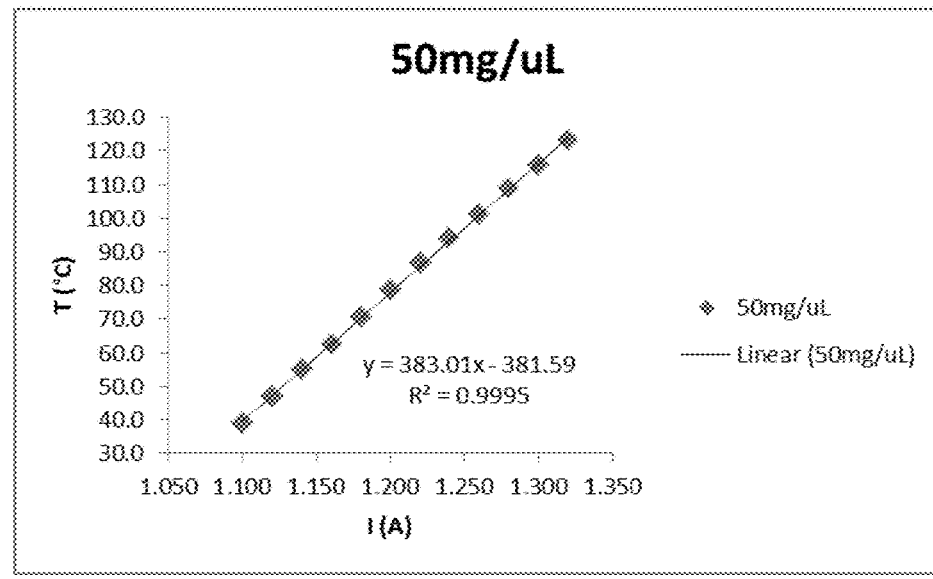
FIG. 9: Heating using magnetic particles dispersed in the qPCR solution according to one aspect of the present invention.

Heating using paramagnetic particles, in which the 'substrate' is suspended into the qPCR solution (see FIG. 1E). Surprisingly, the temperature was stable up to around 130° C. This feature allows setting the target temperature way above 100° C. and thus enabling faster ramp/heating rates. In addition, this mode of heating would be independent of any vibrational features of water i.e. this mode of heating is wavelength-independent and allows to pick a laserdiode based solely on its efficiency and cost (see FIG. 9). At the same time, the paramagnetic particles could be used for the sample preparation process, which proceeds the qPCR.

PREFERRED EMBODIMENTS

Example 1

In one embodiment, the invention is a thermal system for amplification of a nucleic acid sample comprising:
an electromagnetic radiation emitted from a laser diode light source;
an optics manipulation system that splits the light beam from the laser diode and generates spatially distributed multiple light beamlets using optic fibres, collimators/focusers, plate beam splitters, diffraction gratings and mirrors
a substrate positioned in a path of above said light beamlets and configured to absorb the radiated light energy and generate heat energy;
a holding device (reaction compartment) to hold said nucleic acid sample, said holding device in physical contact with the substrate, said holding device configured to transmit the heat from the substrate to the nucleic acid sample; and
the nucleic acid sample containing at least one nucleic acid which undergoes amplification in response to the thermal cycle
a cooling system to cool said substrate and samples to a different temperature setting
Platinum RTD sensors, thermocouples and non-contact thermopile sensors to accurately measure the temperature of the substrate and samples,
A feedback PID control system for the above said thermal management and to produce thermal cycles required for nucleic acid processing such as 95° C. for denaturation and 60° C. for annealing/extension for example.
the nucleic acid sample containing at least one nucleic acid which undergoes amplification in response to the thermal cycle Example 2

The thermal system of Embodiment in Example 1 for amplification of nucleic acid samples further comprising:
additional holding devices (=reaction compartments) to hold additional nucleic acid samples;
additional electromagnetic radiation laser diode light sources;
the above mentioned nucleic acid sample of Embodiment 1 and the addition of nucleic acid samples placed in physical contact with the substrate and spaced apart and thermally communicating with one another via the said substrate; and
the substrate configured to rotate so that separate nucleic acid samples are positioned in a path of radiated light from each electromagnetic source at a time and each thermal cycle experienced by each nucleic acid sample is identical.

Example 3

A thermocycler device comprising:
a detection system;
a fluorescent signal processor connected to said detection system for processing a fluorescent signal detected by said detection system;
a thermal system as defined in Embodiment Example 1 or Embodiment Example 2 above;
optional components such as display, GPS, battery/recharging circuit, WiFi, optical position sensor for detection system, MCU/embedded PC, controller(s) and software for each of those; and
a power source for powering said device.

The device is designed to be used with a Software that: a) interfaces, qPCR data manipulation at the end of the run, log service (GPS), real-time data streaming (WiFi/GSM in combination with dedicated server), healthcare services, GMP compliance, minimum requirement for scientific publications, remote diagnosis function.

Those skilled in the art will appreciate that the invention described herein is susceptible to variations and modifications other than those specifically described. The invention includes all such variation and modifications. The invention also includes all of the steps, features, formulations and compounds referred to or indicated in the specification, individually or collectively and any and all combinations or any two or more of the steps or features.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

The present invention is not to be limited in scope by any of the specific embodiments described herein. These embodiments are intended for the purpose of exemplification only. Functionally equivalent products, formulations and methods are clearly within the scope of the invention as described herein.

The invention described herein may include one or more range of values (eg size, concentration etc). A range of values will be understood to include all values within the range, including the values defining the range, and values adjacent to the range which lead to the same or substantially the same outcome as the values immediately adjacent to that value which defines the boundary to the range.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

While the invention has been described with reference to specific methods and embodiments, it will be appreciated that various modifications and changes may be made without departing from the invention.

The invention claimed is:

1. A device for adjusting the temperature of at least one sample, the device comprising:
   a sample vessel for holding the sample;
   a substrate external to the sample vessel and a laser diode for projecting light onto the substrate, wherein the laser diode is configured to project light onto at least a portion of the substrate such that the substrate absorbs and converts the light energy to thermal energy thereby raising the temperature of the substrate by an amount corresponding to the intensity of the light energy, such that thermal energy is transferred to the sample, wherein the substrate and the laser diode are rotated relative to each other.

2. The device of claim 1 wherein a portion of the substrate that comes into contact with the light has an emissivity value of larger than 0.9 and in particular the portion of the substrate that comes into contact with the light is black and a portion of the substrate that does not come into contact with the light is non-black.

3. The device of claim 1 wherein the substrate is in the form of a ring.

4. The device of claim 1 wherein the substrate is made of metals, alloys, metal composites, ceramics, foams or thermally conductive polymers.

5. The device of claim 1 further comprising one or more optical elements selected from a beam splitter, a diffractive optical element, a mirror, a lens, a light guide or an optical switch is positioned in the path of a light beam between the laser diode and the substrate.

6. The device of claim 1 further comprising at least one of the following: a fan or a blower to remove thermal energy from the substrate, a signal processor for detecting a signal of the sample, a portable battery and a temperature sensor not in contact with the substrate.

7. A device for adjusting the temperature of at least one sample, the device comprising:
   a sample vessel for holding the sample, a substrate external to the sample vessel and a laser diode for projecting light onto the substrate, wherein light is provided as a plurality of beamlets projected onto the substrate at several locations, such that the substrate absorbs and converts the light energy to thermal energy thereby raising the temperature of the substrate by an amount corresponding to the intensity of the light energy, such that thermal energy is transferred to the sample.

8. The device of claim 7, wherein the substrate or laser diode is configured to rotate relative to the other.

9. The device of claim 7 wherein a portion of the substrate that comes into contact with the light has an emissivity value of larger than 0.9 and in particular the portion of the substrate that comes into contact with the light is black and a portion of the substrate that does not come into contact with the light is non-black.

10. The device of claim 7 wherein the substrate is in the form of a ring.

11. The device of claim 7 wherein the substrate is made of metals, alloys, metal composites, ceramics, foams or thermally conductive polymers.

12. The device of claim 7 further comprising one or more optical elements selected from a beam splitter, a diffractive optical element, a mirror, a lens, a light guide or an optical switch is positioned in the path of a light beam between the laser diode and the substrate.

13. The device of claim 7 further comprising at least one of the following: a fan or a blower to remove thermal energy from the substrate, a signal processor for detecting a signal of the sample, a portable battery, and a temperature sensor not in contact with the substrate.

* * * * *